(12) United States Patent
Enten et al.

(10) Patent No.: US 12,007,316 B2
(45) Date of Patent: Jun. 11, 2024

(54) PULSE-MODULATED PERIODIC BACKFLUSH FOR CLEARANCE OF FOULING LAYERS IN DEAD-END FILTRATION SYSTEMS

(71) Applicant: Georgia Tech Research Corporation, Atlanta, GA (US)

(72) Inventors: Aaron C. Enten, Atlanta, GA (US); Todd Sulchek, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 964 days.

(21) Appl. No.: 16/965,111

(22) PCT Filed: Jan. 30, 2019

(86) PCT No.: PCT/US2019/015782
§ 371 (c)(1),
(2) Date: Jul. 27, 2020

(87) PCT Pub. No.: WO2019/152476
PCT Pub. Date: Aug. 8, 2019

(65) Prior Publication Data
US 2020/0363300 A1    Nov. 19, 2020

Related U.S. Application Data

(60) Provisional application No. 62/623,602, filed on Jan. 30, 2018.

(51) Int. Cl.
*G01N 1/34* (2006.01)
*B01D 61/18* (2006.01)
(Continued)

(52) U.S. Cl.
CPC ............... *G01N 1/34* (2013.01); *B01D 61/18* (2013.01); *B01D 61/22* (2013.01); *B01D 63/087* (2013.01);
(Continued)

(58) Field of Classification Search
CPC .................. G01N 1/34; G01N 1/4005; G01N 2001/4088; B01D 61/18; B01D 61/22;
(Continued)

(56) References Cited

U.S. PATENT DOCUMENTS 3,997,447 A * 12/1976 Breton .................. B01D 33/27
210/791
2001/0000895 A1  5/2001 Ilias et al.
(Continued)

OTHER PUBLICATIONS

Enten et. al "Optimizing flux capacity of dead-end filtration membranes by controlling flow with pulse width modulated periodic backflush" Sci Rep 10, 896 (2020). https://doi.org/10.1038/s41598-020-57649-9 (Year: 2020).*
(Continued)

*Primary Examiner* — Liam Royce
(74) *Attorney, Agent, or Firm* — Troutman Pepper Hamilton Sanders LLP; Ryan A. Schneider; Korbin M. Blunck

(57) ABSTRACT

Embodiments of the present disclosure relate generally to dead-end filtration systems and, more particularly, to pulse-modulated periodic backflush systems and methods for clearing fouling layers in dead-end filtration systems. In some embodiments, a controller may control the flow of fluid in the system from cycling from a forward flow to a reverse flow. In some embodiments, the controller may cycle from forward to reverse flow based on a volumetric flow ratio. Embodiments of the present disclosure describe optimal volumetric flow ratios for optimizing the break of cake in a dead-end filtration system. Embodiments of the present
(Continued)

disclosure describe optimal volumetric flow ratios for optimizing recovery percentages of targeted particles.

28 Claims, 10 Drawing Sheets

(51) Int. Cl.
  *B01D 61/22* (2006.01)
  *B01D 63/08* (2006.01)
  *C12M 1/26* (2006.01)
  *C12M 3/00* (2006.01)
  *G01N 1/40* (2006.01)

(52) U.S. Cl.
  CPC ............ *C12M 21/08* (2013.01); *C12M 33/14* (2013.01); *G01N 1/4005* (2013.01); *B01D 2311/16* (2013.01); *B01D 2315/08* (2013.01); *G01N 2001/4088* (2013.01)

(58) Field of Classification Search
  CPC .............. B01D 63/087; B01D 2311/16; B01D 2315/08; C12M 21/08; C12M 33/14
  See application file for complete search history.

(56) References Cited

U.S. PATENT DOCUMENTS

| | | |
|---|---|---|
| 2004/0104171 A1 | 6/2004 | Zeiher et al. |
| 2014/0299532 A1 | 10/2014 | Becker et al. |
| 2016/0046503 A1 | 2/2016 | Hoek et al. |
| 2016/0193569 A1* | 7/2016 | de los Reyes ......... B01D 63/02 210/636 |

OTHER PUBLICATIONS

Yoon et. al. "Clogging-free microfluidics for continuous size-based separation of microparticles". Sci Rep 6, 26531 (2016). https://doi.org/10.1038/srep26531 (Year: 2016).*

International Search Report and Written Opinion from Application No. PCT/US2019/015782 dated Jun. 7, 2019 (14 pages).

Lieleg, et al., "Selective Filtering Particles by the Extracellular Matrix: An Electrostatic Bandpass," Biophysical Journal, vol. 97, Sep. 2009 pp. 1569-1577.

Wikipedia "Diluent," May 30, 2015.

* cited by examiner

PULSE-MODULATED PERIODIC BACKFLUSH FOR CLEARANCE OF FOULING LAYERS IN DEAD-END FILTRATION SYSTEMS

CROSS-REFERENCE TO RELATED APPLICATIONS

This Application claims priority to U.S. Provisional Patent Application No. 62/623,602, filed 30 Jan. 2018, which is hereby incorporated by reference herein in its entirety as if fully set forth below.

STATEMENT REGARDING FEDERALLY SPONSORED RESEARCH OR DEVELOPMENT

This invention was made with government support under Award No. #2T32GM8433-26 awarded by the National Institutes of Health. The government has certain rights in the invention.

FIELD OF THE DISCLOSURE

Embodiments of the present disclosure relate generally to dead-end filtration systems and, more particularly, to pulse-modulated periodic backflush systems and methods for clearing fouling layers in dead-end filtration systems.

BACKGROUND

Filtrations systems and techniques for the isolation of targeted particles and removal of nontargeted particles are standard in both laboratory and clinical settings. This type of sorting process is applied across a wide range of spaces from disease diagnostics, to sample purifications for therapeutics, to cellular isolations for study and treatment of cell and tissue injury. The immense utility of these techniques has sprung the development of a variety of filtration systems. This variety can be summarily organized into two main modalities: labeled filtration and label-free filtration.

Labeled techniques include attaching other particles, such as biomolecules or primers, to the targeted particle in the system. One downside of such techniques is that attaching additional particles to the targeted particles may affect the function of those targeted particles after sorting. This can be particularly problematic when the targeted particles are being sorted for studies, therapeutics, or other treatments. Alternatively, label-free techniques do not involve attaching additional labeling particles to the targeted particles, but instead rely on mechanical properties of the targeted particles, such as size, density, and/or stiffness. The contraindications of labeled techniques have pushed the clinical sorting market away from labeling and towards label-free methods.

Size exclusion is one type of label-free technique that is well established as a method that avoids many of the negative effects of other filtration systems and methods. Two major size-based filtration systems used in laboratory and clinical settings are cross-flow filters and dead-end filters. Cross-flow filtration is a technique wherein the bulk flow from the feed stream runs parallel to the filtration surface, and the filtration occurs primarily via osmotic pressure. Conversely, dead-end systems are fluidic circuits where the filtration surface is set up perpendicular to the feed stream. Accordingly, this means that all particulate in the bulk sample must interact with the filtration surface to complete flow through the circuit.

Both size-based systems have their advantages and disadvantages. The industry utilizes four main metrics to analyze a filtration system's ability to isolate targeted from nontargeted particulate: purity, enrichment factor, recovery percentage, and throughput. An ideal system maintains a high value for each of these four metrics. Cross-flow systems obtain high purity and enrichment factors. However, the throughput and recovery percentage of the systems tend to be significantly lower than other size-based systems due to their parallel flow and osmotic-filtration characteristics-many targeted particles merely pass by the filtration surface instead of passing through the surface.

Dead-end filtration achieves high purity, enrichment factor, and throughput. However, these systems also achieve poor recovery percentage. The perpendicular nature of these systems, where the bulk sample must interact with the filtration surface, causes what is known as membrane fouling. Fouling occurs when a fouling layer and a cake layer forms at one end of the filtration surface as particles build up. This buildup of cake prevents the targeted particles from passing through the filtration surface. As a result, permeate flux will approach zero as cake builds. Dead-end systems are an ideal target for improvement to filtration systems, however. Their enormous enrichment factors, high purity, and high throughput are desirable in the clinical and laboratory settings. What is needed, therefore, are systems and methods that maintain the beneficial characteristics of dead-end filtration but also eliminate the problems associated with particle recovery percentage.

SUMMARY

Embodiments of the present disclosure address these concerns as well as other needs that will become apparent upon reading the description below in conjunction with the drawings. Briefly described, embodiments of the present disclosure relate generally to dead-end filtration systems and, more particularly, to pulse-modulated periodic backflush systems and methods for clearing fouling layers in dead-end filtration systems.

An exemplary embodiment of the present invention provides a filtration system comprising a channel having an inlet and an outlet. The inlet may be configured to receive a suspension comprising a fluid, a plurality of first particles, and a plurality of second particles, the first particles being larger than the second particles. The filtration system may further comprise a membrane positioned between the inlet and the outlet, wherein the membrane is configured to allow at least a portion of the fluid and a portion of the plurality of second particles to permeate through the membrane from the inlet to the outlet and prevent at least a portion of the plurality of first particles from permeating through the membrane from the inlet to the outlet. The filtration may further comprise a controller configured to cycle a flow of the fluid from flowing in a forward direction from the inlet, through the membrane, and to the outlet to flowing in a reverse direction from the outlet, through the membrane, and to the inlet.

In any of the embodiments described herein, for each cycle, a volume of fluid flowing through the membrane in the forward direction may be greater than a volume of fluid flowing through the membrane in the reverse direction.

In any of the embodiments described herein, the controller may cycle the flow of the fluid from the forward direction to the reverse direction based on a volumetric flow ratio, wherein the volumetric flow ratio is equal to $$\frac{V_f}{V_f + V_r},$$

wherein $V_f$ is the volume of fluid flowing through the membrane in the forward direction of a cycle, and Vr is the volume of fluid flowing through the membrane in the reverse direction of the cycle.

In any of the embodiments described herein, the volumetric flow ratio may be from between 0.5 and 1.00.

In any of the embodiments described herein, the volumetric flow ratio may be from between 0.55 and 0.80.

In any of the embodiments described herein, the controller may be configured to vary at least one of a volumetric flow rate of the fluid in the forward direction or a volumetric flow rate of the fluid in the reverse direction from a first cycle to a subsequent second cycle.

In any of the embodiments described herein, the controller may be configured to increase the volumetric flow rate of the fluid in the reverse direction from a first cycle to a subsequent second cycle.

In any of the embodiments described herein, a volumetric flow rate of the fluid in the reverse direction may be greater than a volumetric flow rate of the fluid in the forward direction.

In any of the embodiments described herein, a volumetric flow rate of the fluid in the forward direction may be greater than a volumetric flow rate of the fluid in the reverse direction.

In any of the embodiments described herein, a first side of the membrane proximate the inlet of the channel may comprise a cake layer, the cake layer comprising a portion of the plurality of first particles and a portion of the plurality of second particles, and wherein the flow of the fluid in the reverse direction is configured to break apart at least a portion of the cake layer.

In any of the embodiments described herein, the membrane may comprise at least one of a fibrous membrane, patterned microsieve membrane, pillar membrane, trap membrane, or weir membrane.

In any of the embodiments described herein, the membrane may comprise a tissue.

In any of the embodiments described herein, the tissue may comprise at least one of an extracellular matrix or a bone matrix.

In any of the embodiments described herein, the fluid may comprise whole blood, wherein the first particles are white blood cells and the second particles are red blood cells.

In any of the embodiments described herein, the fluid may comprise a diluting agent.

In any of the embodiments described herein, the second particles may be bacterial cells.

In any of the embodiments described herein, the first particles may be aggregated particulates resulting from a protein conjugation protocol and the second particles may be conjugated microspheres.

In any of the embodiments described herein, the controller may be configured to decrease the volumetric flow ratio in each subsequent cycle.

In any of the embodiments described herein, the controller may be configured to increase the volumetric flow ratio in each subsequent cycle.

In any of the embodiments described herein, the controller may be configured to monitor an amount of the plurality of second particles permeating through the membrane during flow of the fluid in the forward direction of a first cycle, and based on the monitored amount, vary at least one of the volumetric flow ratio, volumetric flow rate in the forward direction, volumetric flow rate in the reverse direction, duration of flow in the forward direction, and a duration of flow in the reversion direction, during a subsequent second cycle.

According to another embodiment of the present invention, a method of filtering particles is provided. The method comprises providing a filtration system comprising a membrane and a channel, the channel having an inlet and an outlet, the membrane positioned in the channel between the inlet and the outlet. The method may further comprise providing a suspension into the inlet of the channel, the suspension comprising a fluid, a plurality of first particles and a plurality of second particles, the first particles being larger than the second particles. The method may further comprise cycling a flow of the fluid through the filtration system between a forward direction in which at least a portion of the fluid flows from the inlet, through the membrane, and to the outlet and a reverse direction in which at least a portion of the fluid flows from the outlet, through the membrane, and to the inlet. When fluid is flowed in the forward direction, at least a portion of the plurality of second particles permeate from the inlet, through the membrane, and to the outlet, and the membrane prevents the plurality of first particles from permeating from the inlet, through the membrane, and to the outlet.

In any of the embodiments described herein, for each cycle, a volume of fluid flowing through the membrane in the forward direction may be greater than a volume of fluid flowing through the membrane in the reverse direction.

In any of the embodiments described herein, the flow of the fluid through the filtration system may cycle between the forward direction and the reverse direction based on a volumetric flow ratio, wherein the volumetric flow ratio is equal to $$\frac{V_f}{V_f + V_r},$$

wherein $V_f$ is the volume of fluid flowing through the membrane in the forward direction of a cycle, and Vr is the volume of fluid flowing through the membrane in the reverse direction of the cycle.

In any of the embodiments described herein, the volumetric flow ratio may be from between 0.5 and 1.00.

In any of the embodiments described herein, the volumetric flow ratio may be from between 0.55 and 0.80.

In any of the embodiments described herein, the volumetric flow ratio may decrease in each subsequent cycle.

In any of the embodiments described herein, the volumetric flow ratio may increase in each subsequent cycle.

In any of the embodiments described herein, a volumetric flow rate of the fluid in the reverse direction may be greater than a volumetric flow rate of the fluid in the forward direction.

In any of the embodiments described herein, a volumetric flow rate of the fluid in the forward direction may be greater than a volumetric flow rate of the fluid in the reverse direction.

In any of the embodiments described herein, the flow of the fluid in the forward direction may form a cake layer about a first side of the membrane proximate the inlet of the channel, the cake layer comprising at least a portion of the plurality of first particles and at least a portion of the plurality of second particles, and wherein the flowing of the fluid in the reverse direction breaks apart at least a portion of the cake layer.

In any of the embodiments described herein, the membrane may comprise at least one of a fibrous membrane, patterned microsieve membrane, pillar membrane, trap membrane, or weir membrane.

In any of the embodiments described herein, the membrane may comprise a tissue.

In any of the embodiments described herein, the tissue may comprise at least one of an extracellular matrix or a bone matrix.

In any of the embodiments described herein, the fluid may comprise whole blood, wherein the first particles are white blood cells and the second particles are red blood cells.

In any of the embodiments described herein, the fluid may comprise a diluting agent.

In any of the embodiments described herein, the second particles may be bacterial cells.

In any of the embodiments described herein, the first particles may be aggregated particulates resulting from a protein conjugation protocol and the second particles may be conjugated microspheres.

In any of the embodiments described herein, the method may comprise decreasing the volumetric flow ratio in each subsequent cycle.

In any of the embodiments described herein, the method may comprise increasing the volumetric flow ratio in each subsequent cycle.

In any of the embodiments described herein, the method may comprise monitoring an amount of the plurality of second particles permeating through the membrane during flow of the fluid in the forward direction of a first cycle. In any of the embodiments described herein, the method may comprise varying, based on the monitored amount, at least one of the volumetric flow ratio, a volumetric flow rate in the forward direction, a volumetric flow rate in the reverse direction, a duration of flow in the forward direction, and a duration of flow in the reversion direction, during a subsequent second cycle.

In any of the embodiments described herein, the method may comprise cycling a flow of the fluid through the filtration system between the forward direction in which a portion of the fluid flows from the outlet, through the membrane, and to the inlet and in the reverse direction in which at least a portion of the fluid flows from the inlet, through the membrane, and to the outlet. When the fluid is flowed in the forward direction, at least a portion of the plurality of second particles may permeate the outlet, through the membrane, and to the inlet.

In any of the embodiments described herein, the volumetric flow ratio may have a linear relationship to a recovery percentage for a portion of the second particles permeating from the inlet, through the membrane, and to the outlet. The method may comprise calculating the recovery percentage of the second particles permeating from the inlet, through the membrane, and to the outlet at a plurality of volumetric flow ratios. The method may comprise identifying a desired permeation amount for a portion of the second particles based on the recovery percentage. The method may comprise calculating a desired volumetric flow ratio based on the linear relationship. The method may comprise adjusting the volumetric flow ratio to equal the desired volumetric flow ratio. The method may comprise recovering the desired permeation amount for the portion of the second particles.

According to another embodiment of the present invention, a method of controlling seed density and uniformity in a profusion bioreactor is provided. The method comprises providing a filtration system comprising a tissue scaffold and a channel, the channel having an inlet and an outlet, the tissue scaffold positioned in the channel between the inlet and the outlet. The method may comprise providing a suspension into the inlet of the channel, the suspension comprising a fluid and a plurality of cells. The method may comprise cycling a flow of the fluid through the filtration system between a forward direction in which at least a portion of the fluid flows from the inlet and through the tissue scaffold, and a reverse direction in which at least a portion of the fluid flows from the outlet and through the tissue scaffold. When fluid is flowed in the forward direction, at least a portion of the plurality of cells may permeate from the inlet and through the tissue scaffold.

In any of the embodiments described herein, for each cycle, a volume of fluid flowing through the tissue scaffold in the forward direction may be greater than a volume of fluid flowing through the tissue scaffold in the reverse direction.

In any of the embodiments described herein, the flow of the fluid through the filtration system may cycle between the forward direction and the reverse direction based on a volumetric flow ratio, wherein the volumetric flow ratio is equal to $$\frac{V_f}{V_f + V_r},$$

wherein $V_f$ is the volume of fluid flowing through the tissue scaffold in the forward direction of a cycle, and $V_r$ is the volume of fluid flowing through the tissue scaffold in the reverse direction of the cycle.

In any of the embodiments described herein, the volumetric flow ratio may be from between 0.5 and 1.00.

In any of the embodiments described herein, the volumetric flow ratio may be from between 0.55 and 0.80.

In any of the embodiments described herein, the volumetric flow ratio may decrease in each subsequent cycle.

In any of the embodiments described herein, the volumetric flow ratio may increase in each subsequent cycle.

In any of the embodiments described herein, a volumetric flow rate of the fluid in the reverse direction may be greater than a volumetric flow rate of the fluid in the forward direction.

In any of the embodiments described herein, the flow the fluid in the forward direction may form a cake layer about a first side of the tissue scaffold proximate the inlet of the channel, the cake layer comprising at least a portion of the plurality of cells, and wherein the flowing the fluid in the reverse direction breaks apart at least a portion of the cake layer.

In any of the embodiments described herein, the tissue scaffold may comprise at least one of an extracellular matrix or a bone matrix.

In any of the embodiments described herein, the method may comprise decreasing the volumetric flow ratio in each subsequent cycle.

In any of the embodiments described herein, the method may comprise increasing the volumetric flow ratio in each subsequent cycle.

In any of the embodiments described herein, the method may comprise cycling a flow of the fluid through the filtration system between the forward direction in which a portion of the fluid flows from the outlet and through the tissue scaffold, and in the reverse direction in which at least a portion of the fluid flows from the inlet and through the tissue scaffold. In any of the embodiments described herein, when fluid is flowed in the forward direction, at least a portion of the plurality of cells permeate the outlet and through the tissue scaffold.

According to another embodiment of the present invention, a method of delivering molecules into a permeated cell is provided. The method may comprise providing a filtration system comprising a membrane and a channel, the channel having an inlet and an outlet, the membrane positioned in the channel between the inlet and the outlet. The method may comprise providing a suspension into the inlet of the channel, the suspension may comprise a cell medium, a plurality of cells, and a plurality of molecules. The system may comprise cycling a flow of the cell medium through the filtration system between a forward direction in which at least a portion of the cell medium may flow from the inlet, through the membrane, and to the outlet and a reverse direction in which at least a portion of the cell medium may flow from the outlet, through the membrane, and to the inlet. The system may comprise causing at least a portion of the plurality of cells to permeate from the inlet, through the membrane, and to the outlet. In some embodiments, the permeation of the permeated cells through the membrane may apply a shear stress to the permeated cells. The system may comprise permeabilizing the permeated cells that pass through the membrane. The system may comprise delivering at least one molecule of the plurality of molecules into one of the permeabilized cells.

In any of the embodiments described herein, for each cycle, a volume of cell medium flowing through the medium in the forward direction may be greater than the volume of cell medium flowing through the membrane in the reverse direction.

In any of the embodiments described herein, the flow of the cell medium through the filtration system may cycle between the forward direction and the reverse direction based on a volumetric flow ratio, wherein the volumetric flow ratio is equal to $$\frac{V_f}{V_f + V_r},$$

wherein $V_f$ is the volume of cell medium flowing through the membrane in the forward direction of a cycle, and $V_r$ is the volume of cell medium flowing through the membrane in the reverse direction of the cycle.

In any of the embodiments described herein, the volumetric flow ratio may be from between 0.5 and 1.00.

In any of the embodiments described herein, the volumetric flow ratio may be from between 0.55 and 0.80.

In any of the embodiments described herein, the volumetric flow ratio may decrease in each subsequent cycle.

In any of the embodiments described herein, the volumetric flow ratio may increase in each subsequent cycle.

In any of the embodiments described herein, a volumetric flow rate of the cell medium in the reverse direction may be greater than a volumetric flow rate of the cell medium in the forward direction.

In any of the embodiments described herein, a volumetric flow rate of the cell medium in the forward direction may be greater than a volumetric flow rate of the cell medium in the reverse direction.

In any of the embodiments described herein, the flow of the cell medium in the forward direction may form a cake layer about a first side of the membrane proximate the inlet of the channel, the cake layer comprising at least a portion of the plurality of cells, and wherein the flowing of the cell medium in the reverse direction breaks apart at least a portion of the cake layer.

In any of the embodiments described herein, the membrane may comprise a fibrous membrane, patterned microsieve membrane, pillar membrane, trap membrane, or weir membrane.

In any of the embodiments described herein, the membrane may comprise a tissue.

In any of the embodiments described herein, the tissue may comprise at least one of an extracellular matrix or a bone matrix.

In any of the embodiments described herein, the membrane may comprise microchannels.

In any of the embodiments described herein, the plurality of molecules may comprise at least one of macromolecules, nanoparticles, sugars, plasmids, mRNA, enzymes, nucleases, DNA, RNP, antibodies, beads, viruses, immune cells, stem cells, stromal cells, or therapeutic cells.

In any of the embodiments described herein, the volumetric flow ratio may decrease in each subsequent cycle.

In any of the embodiments described herein, the volumetric flow ratio may have a linear relationship to a recovery percentage for the permeated cells. The method may comprise calculating the recovery percentage of the permeated cells permeating from the inlet, through the membrane, and to the outlet at a plurality of volumetric flow ratios. The method may comprise identifying a desired permeation amount for a portion of the permeated cells based on the recovery percentage. The method may comprise calculating a desired volumetric flow ratio based on the linear relationship. The method may comprise adjusting the volumetric flow ratio to equal the desired volumetric flow ratio. The method may comprise recovering the desired permeation amount for the portion of permeated cells.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE FIGURES

Reference will now be made to the accompanying figures and diagrams, which are not necessarily drawn to scale, and wherein.

DETAILED DESCRIPTION

Figure 1A:
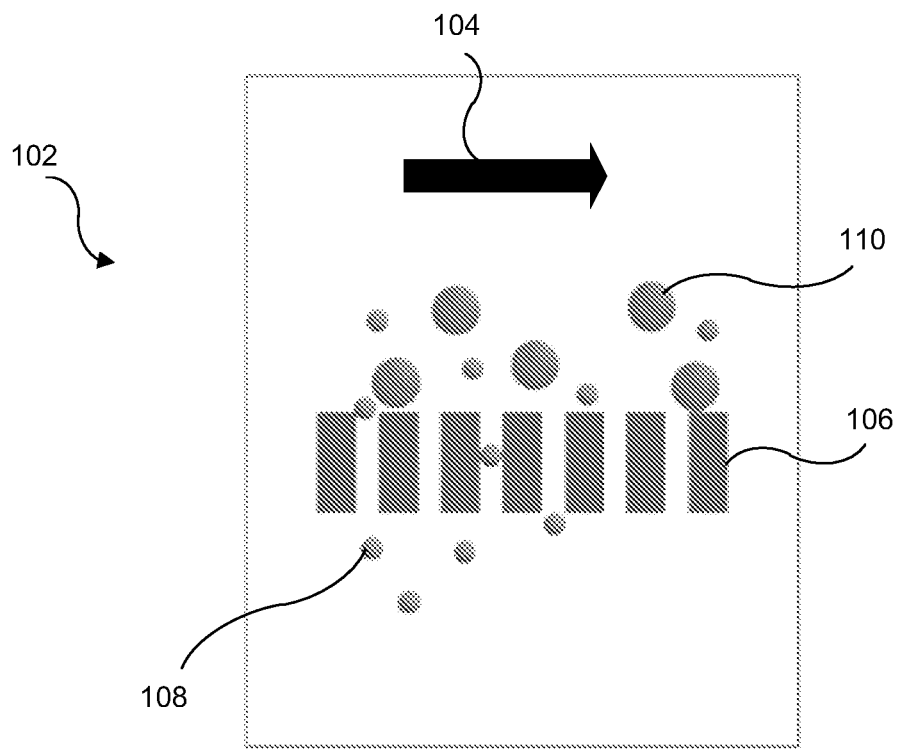
FIG. 1A is a representation of the flow of fluid and particles through a cross-flow filtration system, in accordance with some embodiments of the present disclosure.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an" and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. In particular, the presently disclosed subject matter is described in the context of pulse-modulated periodic backflush for dead-end filtration systems. The present disclosure, however, is not so limited and can be applicable in other contexts. For example, some embodiments of the present disclosure may improve the functionality of other filtration systems, including but not limited to cross-flow filtration systems, other size-based filtration systems, or any other filtration system that may comprise or create a fouling or cake layer. Additionally, although some embodiments of the present disclosure describe filtering biological particles, it will be understood that the present technologies are not limited to biological particles. For example, the presently disclosed technologies may improve the filtration and sorting of any particles that may be used within the filtration systems described herein. These embodiments are contemplated within the scope of the present disclosure. Accordingly, when the present disclosure is described in the context of pulse-modulated periodic backflush for dead-end filtration systems, it will be understood that other embodiments can take the place of those referred to.

Figure 1B:
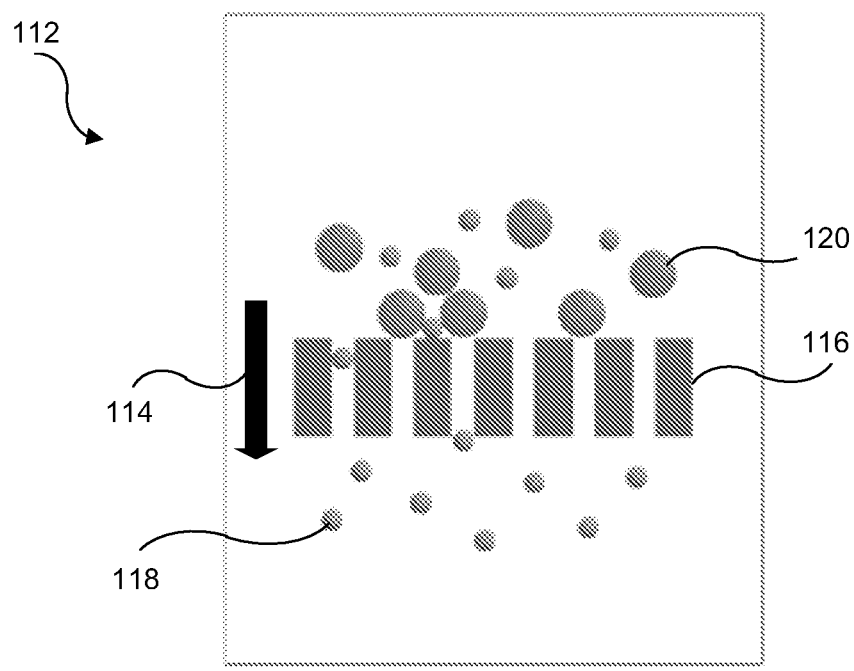
FIG. 1B is a representation of the flow of fluid and particles through a dead-end filtration system, in accordance with some embodiments of the present disclosure.

As described above, several size-based, label-free filtration systems are currently used within laboratory and clinical settings. Two popular systems within this category include cross-flow filtration systems and dead-end filtration systems. FIG. 1A is a representation of the flow of fluid and particles through a cross-flow filtration system 102, according to some embodiments. The fluid flow 104 in a cross-flow filtration system 102 runs parallel to the filtration surface 106. The separation of targeted particles 108 from nontargeted particles 110 occurs primarily via osmotic pressure through the filtration surface 106. FIG. 1B is a representation of the flow of fluid and particles through a dead-end filtration system 112, according to some embodiments. The fluid flow 114 in a dead-end filtration system 112 runs perpendicular to the filtration surface 116. Accordingly, both targeted particles 118 and nontargeted particles 120 in the bulk sample must interact with the filtration surface 116 to complete flow through the system. The term "bulk" within this disclosure refers to the suspension within the filtration system. For example, the bulk flow through a system refers to the flow of a suspension through the system, the suspension comprising a fluid and any number of particles suspended within the fluid. As will be discussed in more detail herein, in some embodiments, the filtration surface may comprise a membrane.

Both size-based systems have their advantages and disadvantages. The industry utilizes four main metrics to analyze a filtration system's ability to isolate targeted from nontargeted particulate: purity, enrichment factor, recovery percentage, and throughput. Purity is a metric used to measure the percentage of targeted particles 108/118 in the output of a system compared to total particulate in that system (i.e., the total of targeted particles 108/118 plus nontargeted particles 110/120 in the system). Enrichment factor is a ratio of ratios that shows the proportion of targeted 108/118 to nontargeted 110/120 particles in the output compared to the initial sample being processed at the input. Enrichment factor ranges from 0 to infinity. A value of 0 implies the permeate (or the recovered particles in the output) contains the same proportion of targeted to nontargeted particulate as what was supplied to the system, thus showing no isolation. A value of infinity would result from perfect permeate purity starting with any amount of contamination. Enrichment factor does not provide any indication of input or permeate concentration or quantity; this is determined by recovery percentage. Recovery percentage provides the number of targeted particles 108/118 at the output compared to what was initially supplied at the input. Throughput is a measure of the output quantity of targeted particles 108/118 as a function of processing time.

An ideal system maintains a high value for each of these metrics; however, different filter types can trade off performance in one of these metrics for performance in another. For example, cross-flow filtration systems 102 may obtain high purity and high enrichment factors, but the throughput and recovery percentage tend to be significantly lower than other size-based systems due to their parallel flow 104 and osmotic-filtration characteristics. Dead-end filtration systems 112 may also achieve high purity, enrichment factors, and throughput, yet the systems may also achieve poor recovery percentage. The perpendicular nature of these systems, where the bulk sample must interact with the filtration surface 116, causes what is known as membrane fouling. This fouling decreases the recovery percentage over time.

Figure 2:
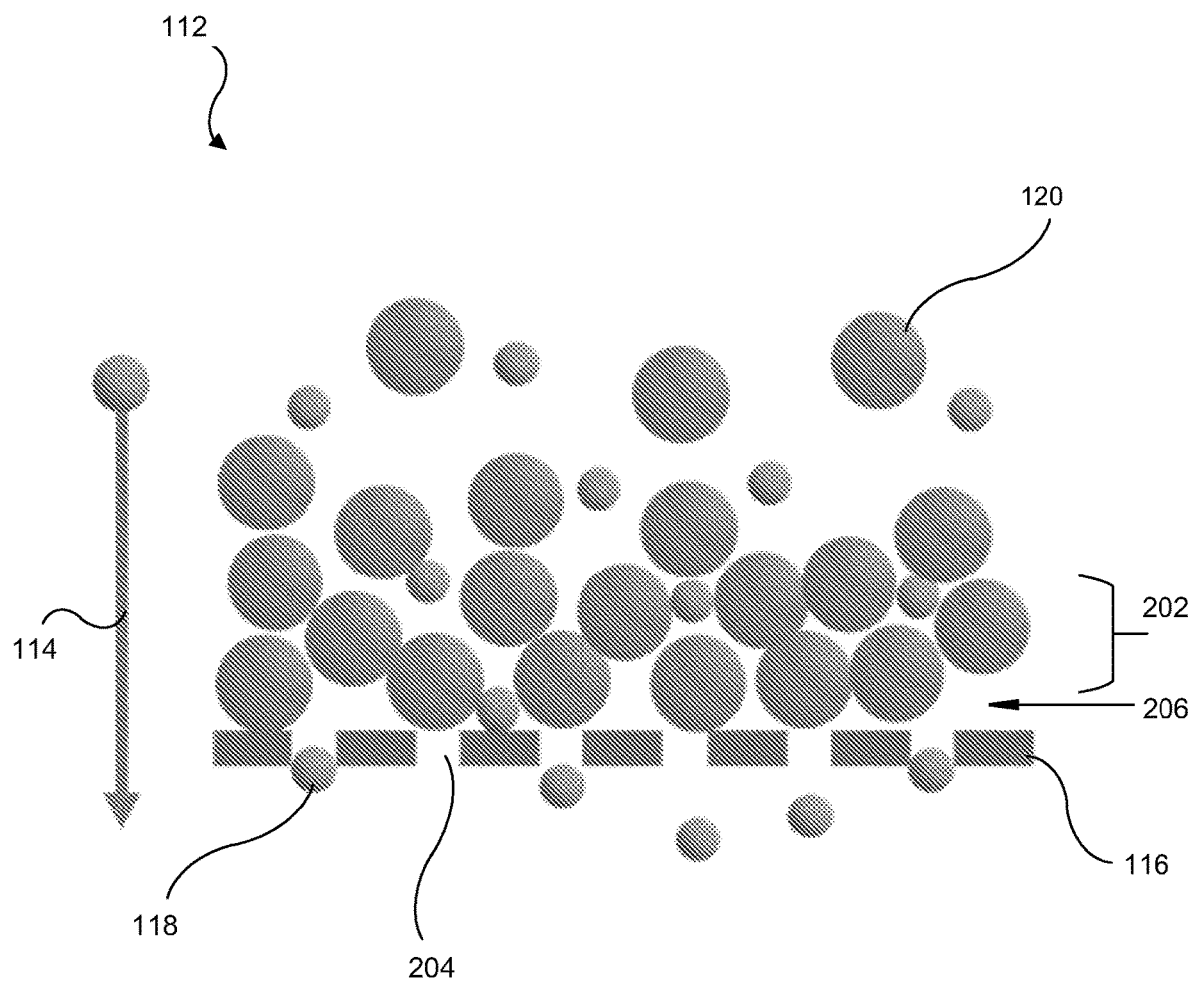
FIG. 2 depicts the formation of a cake layer in a dead-end filtration system, in accordance with some embodiments of the present disclosure.

FIG. 2 depicts the formation of a cake layer 202 in a dead-end filtration system 112, according to some embodiments. In a dead-end filtration system 112, fouling of filtration surface 116 can be caused by pores or openings 204 within the surface becoming blocked. The first layer of blocking is what is known as the fouling layer 206. As more and more particles 118/120 build upon the fouling layer 206, a cake layer 202 grows on the filtration surface 116. As will be appreciated, in the field of filtration devices, the terms "fouling layer," "cake," and "cake layer" may be used interchangeably, and all mean the buildup of particles 118/120 along the filtration surface 116. Accordingly, throughout this disclosure, the terms "fouling layer," "cake," and "cake layer" are used interchangeably. As more and more particles 118/120 add to the cake layer, the flux of targeted particles 118 through the filtration surface 116 decreases exponentially.

Figure 3:
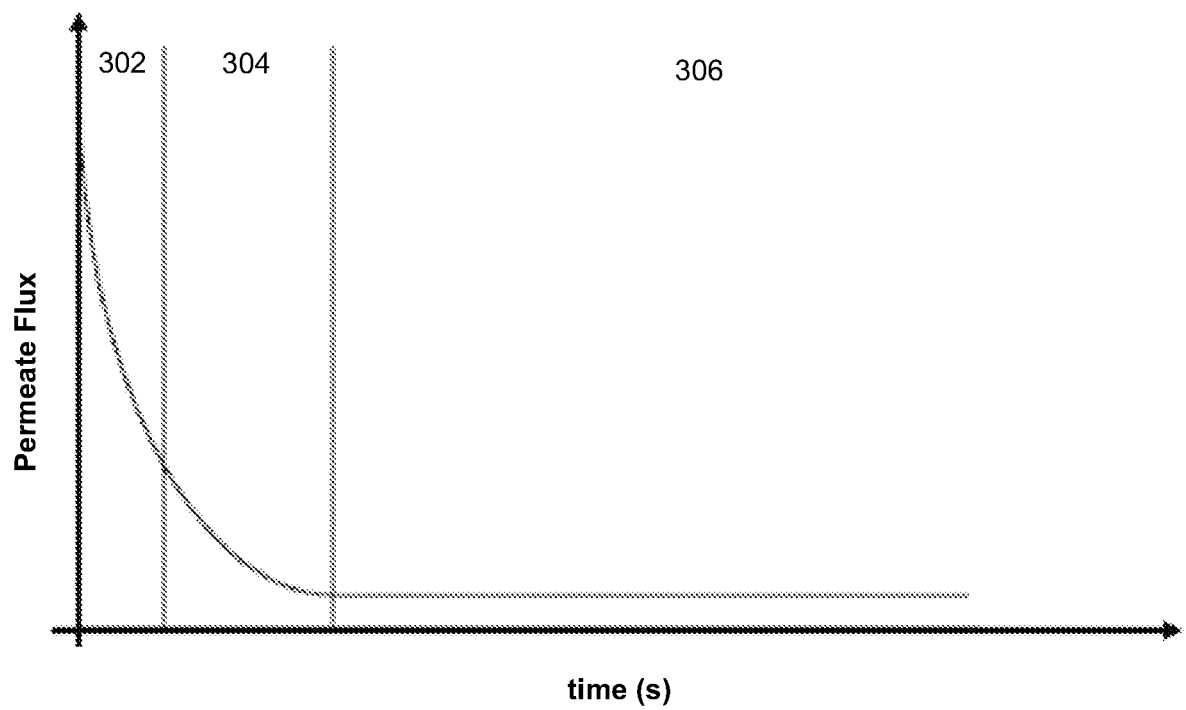
FIG. 3 is an example representation of the exponential decay of permeate flux over a period of time within a dead-end filter, in accordance with some embodiments of the present disclosure.

FIG. 3 is an example representation of the exponential decay of permeate flux over a period of time within a dead-end filter, according to some embodiments. The graph shows the three phases of fouling. The first phase 302 is a period of rapid decline of permeate flux through the filtration surface. The second phase 304 is a period of tapering, where the decline in flux is steadier. However, as seen in the graph, a third phase 306 exists wherein the permeate flux will asymptotically approach zero as cake builds.

Dead-end filtration systems remain popular among laboratory and clinical settings. Despite their limitations with respect to recovery percentage, their purity and enrichment factors remain some of the highest in the industry. Accordingly, the systems are an ideal target for improvement so as to maintain the system's desirable attributes and to increase the recovery percentage for the systems.

Figure 4:
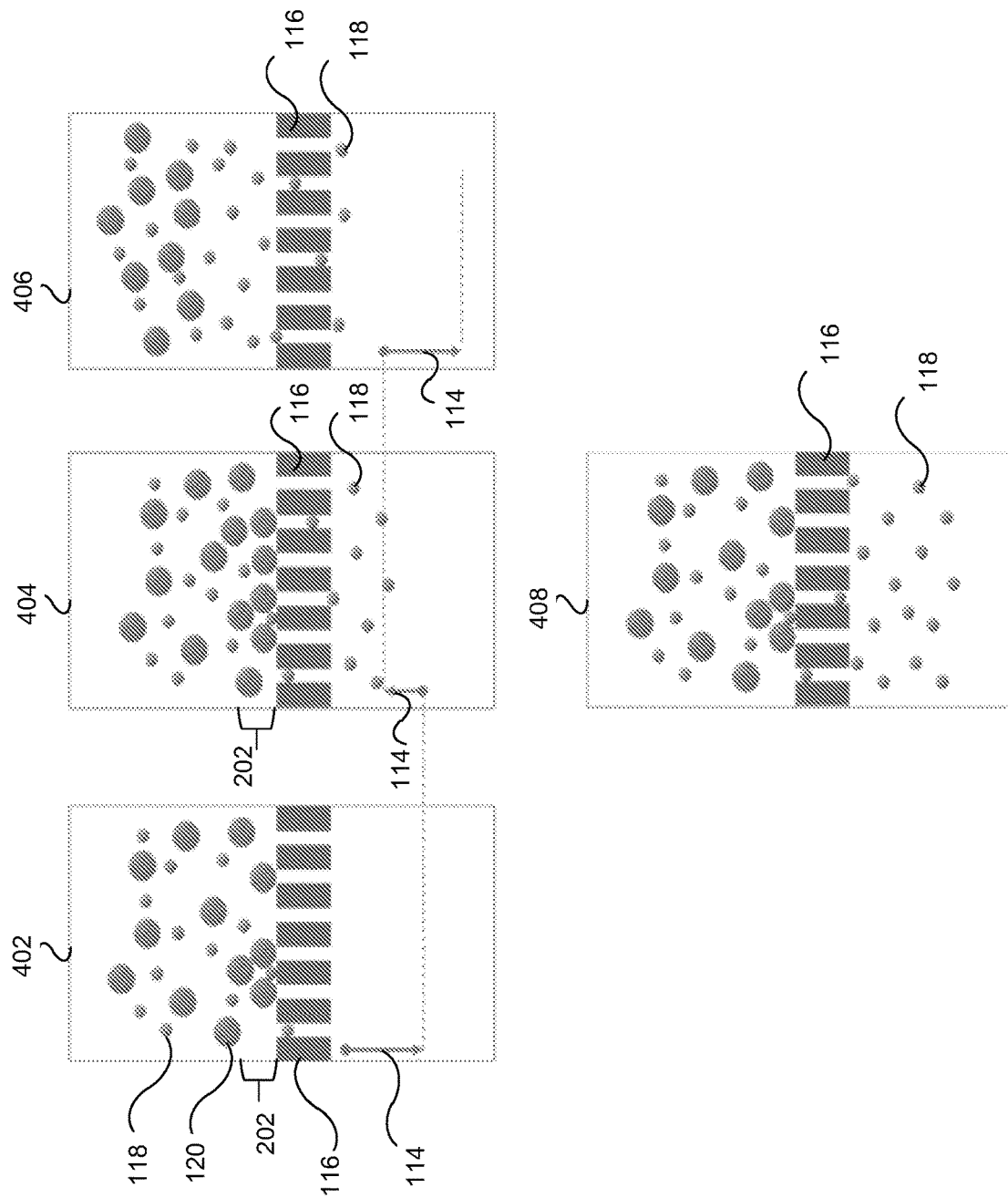
FIG. 4 is a representation of using pulse-modulated periodic backflush for breaking apart a cake layer, in accordance with some embodiments of the present disclosure.

The technologies disclosed herein improve dead-end filtration systems by applying what may be referred to as pulse-modulated (PM) periodic backflush, which is a system and method for breaking apart the cake formed along the filtration surface. FIG. 4 is a representation of PM periodic backflush for breaking apart a cake layer, according to some embodiments of the present disclosure. The first stage 402 of PM periodic backflush is a forward flush. In other words, in the first stage 402, the bulk flow travels through the filtration surface 116 as it would in an ordinary dead-end filtration system. As the bulk flow continues through the filtration surface 116, a cake layer 202 comprising targeted 118 and nontargeted particles 120 will form along one end of the filtration surface 116.

The next stage 404 of PM periodic backflush is an initiation of backflush through the system. The bulk flow of the system is reversed and passed back through the filtration surface 116. This reverse flow breaks apart the cake layer 202 that formed during the period of forward flow. The breaking apart of the cake layer 202 also causes a reintegration of the particles 118/120 into the bulk flow. As can be seen in FIG. 4, the reverse flow stage 404 cases some negative flux of the targeted particles 118 (i.e., back through the filtration surface). However, the degree of negative flux depends on the volume of fluid that passes in a forward direction as compared to a volume of fluid that passes in a reverse direction. This difference in volume will be discussed in greater detail herein.

The next stage 406 of PM periodic backflush is a re-initiation of forward flow through the filtration surface 116. As can be seen in FIG. 4, during the re-initiation stage 406, more targeted particles 118 have passed beyond the filtration surface than in the original forward-flow stage 402. Also, during the re-initiation stage 406, the flux can continue again until a new cake layer is formed. The next stage 408 indicates that the previous stages—forward flow, reverse flow, forward flow—are repeated periodically in this order to improve flux and increase permeation and recovery percentage of targeted particles 118.

In some embodiments, this cycling of forward flow, to reverse flow, to forward flow can be characterized as a square wave. As will be appreciated, a square wave is an appropriate representation of a binary system (on/off or, as in this case, forward/reverse). The positive part of a cycle is representative of forward flow and the negative part of a cycle is representative of reverse flow.

Figure 5:
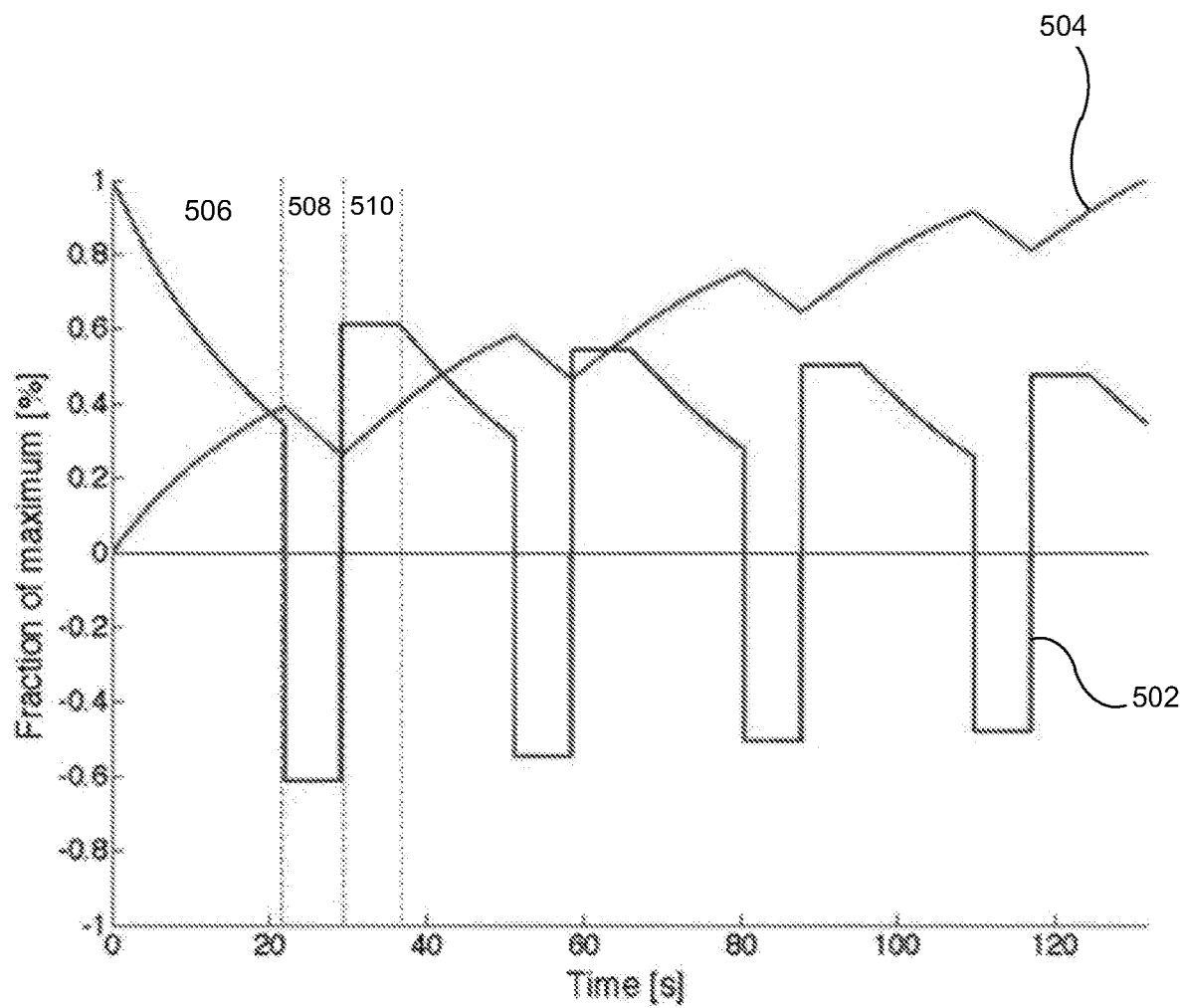
FIG. 5 is a model depicting the square-wave characteristics of pulse-modulated periodic backflush, in accordance with some embodiments of the present disclosure.

FIG. 5 is a model depicting the square-wave characteristics of PM periodic backflush, according to some embodiments of the present disclosure. As described above, as more and more particles add to a cake layer in a dead-end filtration system, the flux of targeted particles through the filtration surface decreases exponentially. The model in FIG. 5 depicts how PM periodic backflush, with its square-wave characteristics, affect this exponential decrease in permeate flux. The solute, or fluid, flowing through the system is represented by the square-wave flow profile 502. The effect of this fluid-flow profile 502 on the mass of the permeate (i.e., targeted particles) 504 recovered through the filtration system is also plotted.

The model in FIG. 5 shows that cycling from forward, to reverse, to forward flow can be divided into three regions. The first region 506 is a period of exponential decay associated with forward filtration. This exponential decay is expected in a typical forward-flowing dead-end filtration system. As the fluid-flow profile 502 decreases as cake builds, the permeation rate for the mass of targeted particles 504 permeating through the system also decreases. The second region 508 is a period of reverse flow. As can be seen, the reverse fluid-flow profile 502 corresponds to a negative flux of targeted particles 504. The third region 510 is a period of near ideal forward flush. This is shown in the model as a flat fluid-flow profile 502. The flat fluid-profile 502 may be the result of fluid flowing freely through the system because the cake layer is no longer present—the particles that previously formed the cake layer have been re-integrated into the bulk flow. The third region 510 also shows a steady increase in the mass of targeted particles 504 permeating through the dead-end filtration system, as the targeted particles also are not restricted by a cake layer.

Important features of the square-wave-like PM periodic backflush is the volume of fluid flow in a forward cycle and the volume of fluid flow in a reverse cycle. As can be seen in the model in FIG. 5, when the fluid-flow profile 502 is in the reverse direction (negative flux), a portion of the mass of targeted particles 504 trends in a reverse direction (i.e., the targeted particles pass back through the filtration system). Therefore, an optimal ratio of forward flow to reverse flow is necessary to optimize permeate flux through the filter. The volume of fluid flow in a forward cycle and the volume of fluid flow in a reverse cycle also directly relate to the amount of cake build-up and break-up. For example, if the volume of flow in the forward direction is large, then a large cake layer will inherently build along the filtration surface. Accordingly, the volume of flow in the reverse direction must be great enough to break apart the cake and re-integrate the particles into the bulk flow. Therefore, an optimal ratio of forward flow to reverse flow is necessary to optimize cake break-up.

The ratio of one cycle of forward flow to one cycle of reverse flow is defined as the system's volumetric flow ratio. The volumetric flow ratio is represented by the equation:

$$\phi = \frac{V_f}{V_f + V_r}$$

Here, $\phi$ is the volumetric flow ratio, $V_f$ is the volume of fluid flowing through the filtration surface in the forward direction over one cycle, and $V_r$ is the volume of fluid flowing through the filtration surface in the reverse direction over a cycle. A $\phi$ of 1.00, $V_f = V_f + V_r$, constitutes continuous forward flow with no reverse flow and is subject to standard exponential decay in flux as fouling occurs, as described above. Comparatively, a $\phi = 0.50$, $V_f = V_r$, has the volumetric flow in the forward direction over a cycle equal to the volumetric flow in the reverse direction over a cycle. Therefore, with a $\phi = 0.50$, no net processing would occur because the flux through the filtration surface would be equal to the flux back through the filtration surface.

A comparison can be made between the volumetric flow ratio and to duty cycle. Duty cycle is a term that refers to the time occupied by the cycle of operation of a machine or other device, especially as a percentage of available time. This is a metric used by mechanical and electrical engineers to define the percent of a period that a machine or waveform remains in the 'on' or functioning state compared to the total period or operating time in a recurring cycle. Pulse modulation of backflush is a technique that varies the volumetric flow ratio (or the duty cycle of the square wave described above) to achieve a desired effect. For example, the volumetric flow ratio $\phi$ refers to the percent of a period that the filtration system is in the "forward volumetric flow" state compared to the total period in a recurring cycle. A period in a PM system is a single cycle of forward flow plus a single cycle of reverse flow.

Figure 6A:
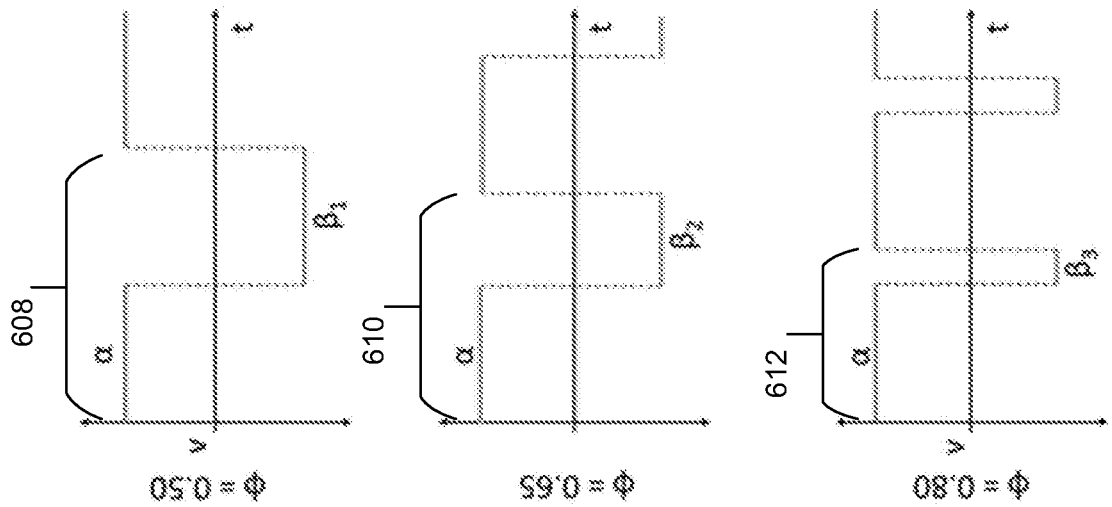
FIG. 6A is a representation of a system with a fixed reverse flow volume β and a variable forward flow volume α, in accordance with some embodiments of the present disclosure.
Figure 6B:
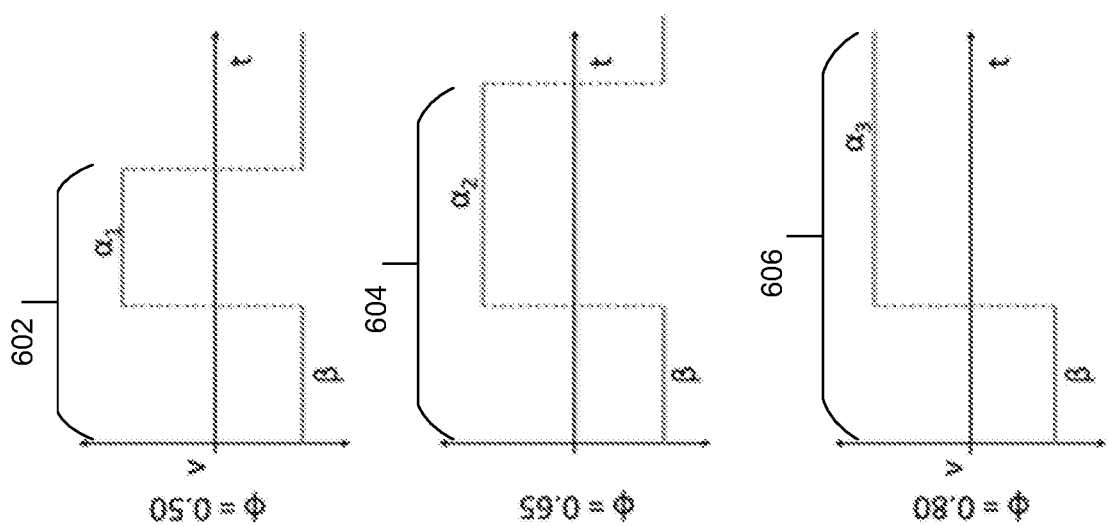
FIG. 6B is a representation of a system with a fixed forward flow volume α and a variable reverse flow volume β, in accordance with some embodiments of the present disclosure.

FIGS. 6A and 6B are example representations of altering the forward flow volume or reverse flow volume to adjust the volumetric flow ratio, according to an exemplary embodiment of the present disclosure. FIG. 6A is a representation of a system with a fixed reverse flow volume β and a variable forward flow volume α, according to some embodiments of the present disclosure. The top chart represents a volumetric flow ratio of 0.50. In other words, over a period 602 of one reverse cycle R to one forward cycle $\alpha_1$, 50% of the total volume flux is in the forward direction. As described above, this embodiment would net zero particle recovery. The next chart represents a volumetric flow ratio of 0.65. Over a period 604 of one reverse cycle β to one forward cycle $\alpha_2$, 65% of the total volume flux is in the forward direction. The bottom chart represents a volumetric flow ratio of 0.80. Over a period 606 of one reverse cycle β to one forward cycle $\alpha_3$, 80% of the total volume flux is in the forward direction.

FIG. 6B is a similar representation, but in these set of charts the system has a fixed forward flow volume α and a variable reverse flow volume β, according to some embodiments of the present disclosure. The top chart of FIG. 6B represents a volumetric flow ratio of 0.50. In other words, over a period 608 of one forward cycle α to one reverse cycle $\beta_1$, 50% of the total volume flux is in the forward direction. As described above, this embodiment would net zero particle recovery. The next chart represents a volumetric flow ratio of 0.65. Over a period 610 of one forward cycle α to one reverse cycle $\beta_2$, 65% of the total volume flux is in the forward direction. The bottom chart represents a volumetric flow ratio of 0.80. Over a period 612 of one forward cycle α to one reverse cycle $\beta_3$, 80% of the total volume flux is in the forward direction.

In some embodiments, the changes to the volumetric flow ratio may be achieved as shown in FIGS. 6A and 6B. Namely, the volumetric flow ratio may be altered by changing how long the system is flowing in that direction over a period of time. In other embodiments, other parameters may be changed besides time of flow. In some embodiments the volumetric flow rate in either the forward direction or the reverse direction may be altered. For example, a volumetric flow ratio $\phi$ of 0.5 may be achieved by flowing fluid in a forward direction at a first velocity for a set amount of time, and then flowing fluid in a reverse direction at a faster velocity for a shorter amount of time. In this embodiment, the result is the same, the volume flux is equal in forward and reversed directions, but the reverse direction achieved the volume flux in a shorter period of time due to the faster velocity. One way to conceive this embodiment would be to increase the amplitude of the reverse cycle β in any of the charts in FIGS. 6A and 6B. It is conceived that either the forward flow or reverse flow may have a greater flow rate (velocity) in any embodiment described herein.

EXPERIMENTAL SECTION

As described above, an optimal volumetric flow ratio ϕ of forward flow to reverse flow is necessary to optimize permeate flux through the filter. Additionally, an optimal volumetric flow ratio ϕ of forward flow to reverse flow is necessary to optimize cake break-up. The following section presents the results of testing PM periodic backflush to identify the optimal range of forward to reverse flow to obtain these results.

The experiments were conducted with Pall Acrodisc syringe filters with Versapor (hydrophilic polypropylene). All filters had a diameter of 25 mm and functional cross-sectional area of approximately 2.8 $cm^2$. A custom syringe actuator was constructed to inject preprogrammed PM pressure waveforms (e.g., the forms shown in FIGS. 6A and 6B). The filtration system, composed of a linear actuator, syringe holster, TMP measurement sensor, and magnetic mixer, was mounted vertically. A feed reservoir for holding the suspension was open to atmospheric pressure. The linear actuator acted as a controller capable of alternating the flow from a forward direction to a reverse direction through the filter. The system was connected to a custom user interface allowing the user to set fluid velocity, pulse duration, volumetric flow ratio ϕ, and frequency.

The actuator executed syringe displacements in increments with a minimum resolution of 0.23 μL when using a 3 mL BD syringe. The software recorded inputs of actuator speed, volumetric flow ratio, gross volume exchange, and total volume of sample to process. All experiments were conducted at a positive and negative absolute flow rate of 4.55 mL/min. The system included a reservoir capable of holding up to 10 mL of suspension. The system could measure transmembrane pressure at a sample rate of 50 Hz.

The particles used in the system included a plurality of first particles having a diameter of 7.32 μm and a plurality of second particles having a diameter of 2.19 μm. The first and second particles were initially mixed together to create a suspension. The effect of volumetric flow ratio on recovery percentage, throughput, and enrichment factor was explored by conducting experiments with a fixed reverse flow volume (as seen in FIG. 6A) and a fixed forward flow volume (as seen in FIG. 6B).

Figure 7A:
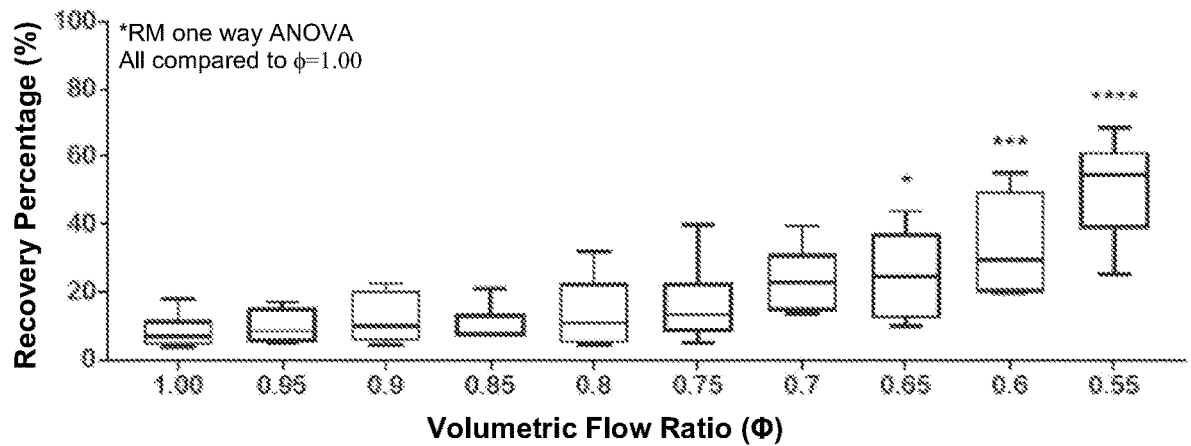
FIG. 7A is the results for recovery percentage in an experiment conducted in a fixed reverse flow system.

FIG. 7A is the results for recovery percentage in an experiment conducted in a fixed reverse flow system. The recovery percentage of the second particles were calculated over a range of volumetric flow ratios from 1.0 (all forward flow) to 0.55. The recovery percentage significantly (pairwise comparison with t-test p<0.0001) increased from a median of 7.11% to 54.73%, for ϕ=1.0 and 0.55, respectively. This shows a 7-fold increase in recovery percentage from full-forward flow to a volumetric flow ratio of 0.55 (i.e., wherein 45% of the total volume flux is in the reverse direction over a period). FIG. 7A also shows that recovery percentage follows a bi-linear function with a region of little to no gain from ϕ=1.0 to 0.8 followed by a region of linear gain from ϕ=0.8 to 0.55. This linear relationship between volumetric flow ratio and recovery percentage provides a platform wherein the user can achieve a desired recovery percentage by selecting the volumetric flow ratio that corresponds to the desired recovery percentage.

Figure 7B:
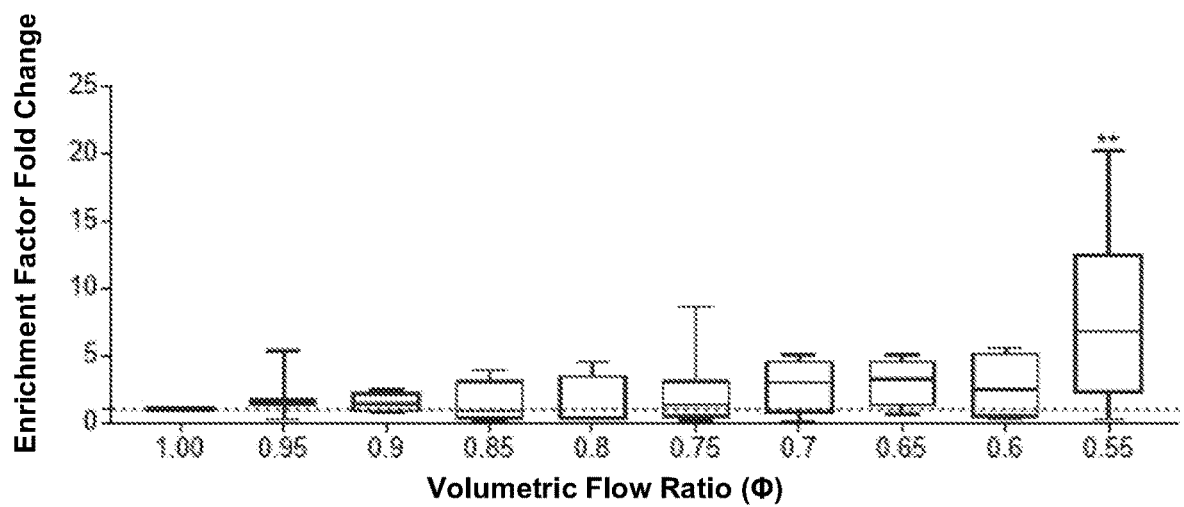
FIG. 7B is the results for enrichment factor in an experiment conducted in a fixed reverse flow system.

FIG. 7B is the results for enrichment factor in an experiment conducted in a fixed reverse flow system. The results show enrichment significantly improved (p<0.01) as ϕ approached 0.55, increasing from an average of 567.3 to 3374.8 for ϕ=1.0 and 0.55, respectively. The increasing values of enrichment indicates an increasing effectiveness of processing. In other words, the increased enrichment factor shows an increased recovery percentage for the targeted particles in the output with no significant change in nontargeted particles in the output.

Figure 8:
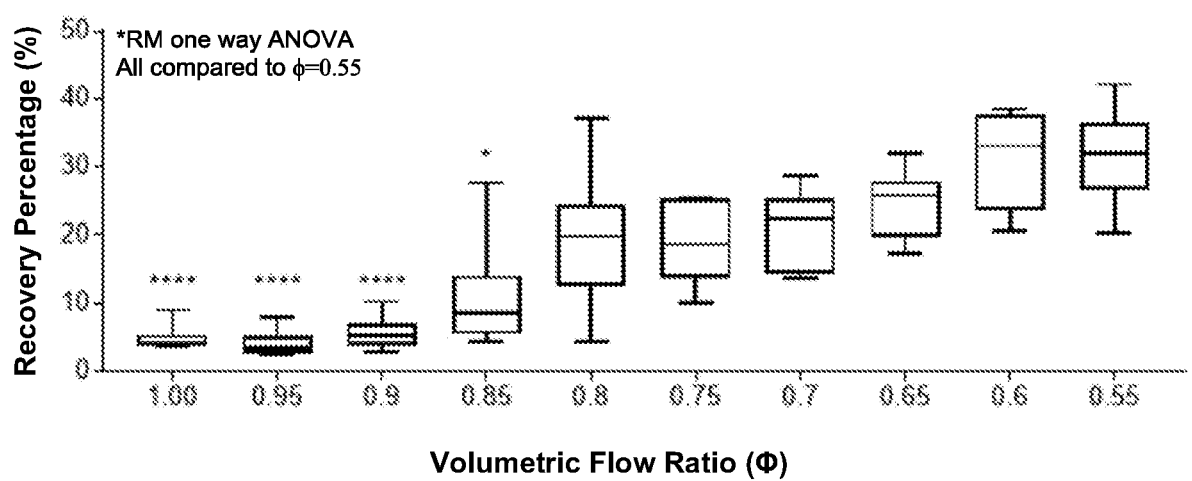
FIG. 8 is the results for recovery percentage in an experiment conducted in a fixed forward flow system.

FIG. 8 is the results for recovery percentage in an experiment conducted in a fixed forward flow system. The results for fixed forward flow are similar to the results above for fixed reverse flow. The results indicate that an optimal recovery percentage exists as the volumetric flow ratio approaches 0.55.

Figure 9:
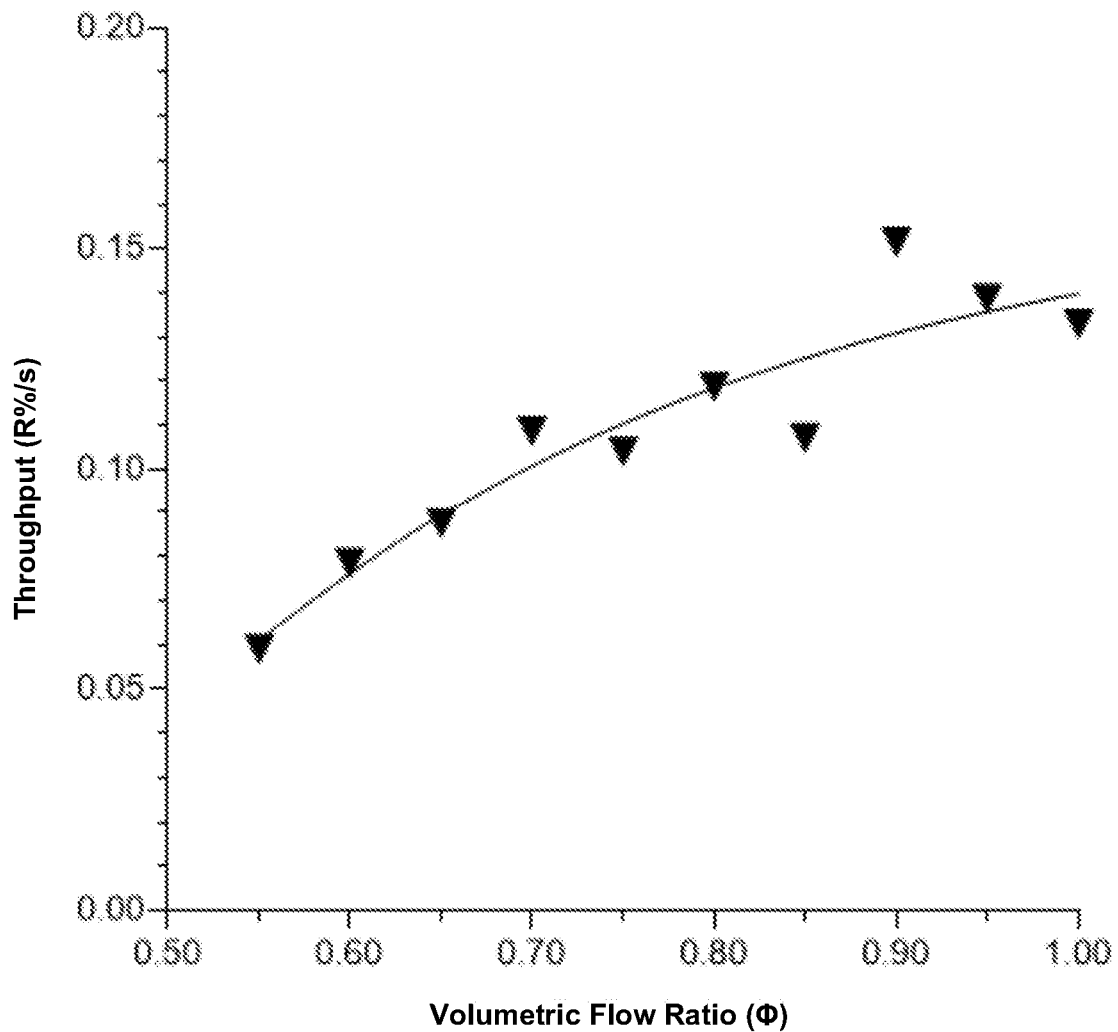
FIG. 9 is the results for change in throughput of the targeted particles over a change in volumetric flow ratio.

FIG. 9 shows the results for the change in throughput of the targeted particles over a change in volumetric flow ratio. As would be expected, as the volumetric flow ratio ϕ approaches 0.50, there is a diminishing rate of return for the throughput. The results show a 44% reduction in throughput as duty cycle decreases from 1.00 to 0.55.

The results of these findings show that an optimal volumetric flow ratio can be determined to (i) optimize permeate flux through a dead-end filtration system and (ii) optimize cake break-up. Furthermore, these findings also indicate that the linear relationship between volumetric flow ratio and recovery percentage may be used advantageously to create a system capable of recovering a desired mass of targeted particles.

Example Use Cases

Figure 10:
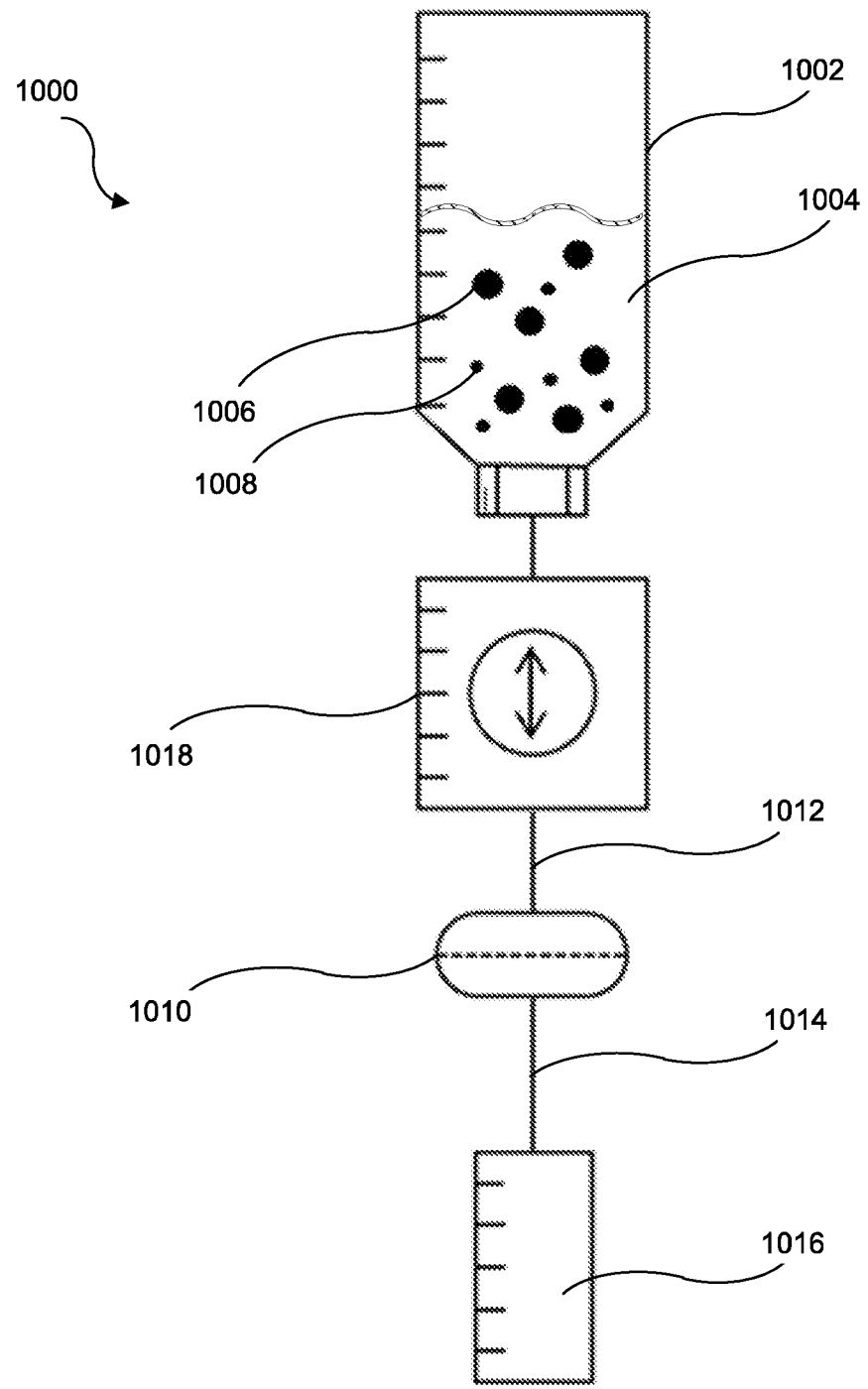
FIG. 10 is an exemplary filtration system in which pulse-modulated period backflush may be realized, in accordance with some embodiments of the present disclosure.

FIG. 10 is an exemplary filtration system in which pulse-modulated periodic backflush may be realized, according to an exemplary embodiment of the present disclosure. In some embodiments, a PM dead-end filtration system 1000 may comprise a reservoir 1002. A reservoir 1002 may be a tank, syringe, fluid bag, cylinder, or any other device that may hold fluid and a plurality of particles. In some embodiments, the reservoir 1002 may be open to atmospheric pressure; in some embodiments, the reservoir 1002 may be a closed system.

In some embodiments, the reservoir 1002 may hold a suspension 1104. The suspension 1104 may comprise a fluid and any of the particles described herein. For example, the suspension 1104 may comprise one or more first particles 1006 and/or one or more second particles 1108. In some embodiments, the first particles 1006 may be larger in size than the second particles 1008. In some embodiments, the first particles 1006 may be any of the nontargeted particles 120 described throughout this disclosure; the second particles 1008 may be any of the targeted particles 118 described throughout this disclosure. In some embodiments, the fluid may comprise whole blood, the first particles 1006 may be white blood cells, and the second particles 1008 may be red blood cells. In some embodiments, the fluid may further comprise a diluting agent. For example and not limitation, in an embodiment wherein the fluid comprises whole blood, a diluent such as phosphate buffered saline, plasma, or any combination thereof, may be added to the suspension 1104. In some embodiments, the second particles 1008 may comprise bacterial cells. In this embodiment, the PM dead-end filtration system 1000 may be removing bacterial cells from a biological sample. In some embodiments, the first particles 1006 may be aggregated particulates resulting from a protein conjugation protocol and the second particles 1008 may be conjugated microspheres. Any other combination of fluid and particles is conceived for use within a PM dead-end filtration system 1000 system.

In some embodiments, the PM dead-end filtration system 1000 may comprise a membrane 1010. The membrane 1010 may be the filtration surface 116 described in FIG. 1B. In some embodiments, the membrane 1010 may be a fibrous or porous filter, such as the Pall Acrodisc filter used in the experimentation described above. The membrane 1010 may be any fibrous filter that may be used for size-based filtration, for example and not limitation a cellulose filter. In some embodiments, the membrane 1010 may be a patterned microsieve membrane. In some embodiments, the membrane 1010 may be a pillar membrane, trap membrane, and/or weir membrane. In some embodiments, the membrane 1010 may be a tissue, as will be described in more detail herein. The tissue of the membrane 1010 may be an extracellular matrix, bone matrix, or any other tissue, as will be appreciated. The bone matrix may be decellularized bone matrix or a sample of bone comprising already-seeded cells. Any other membrane 1010 or combination of membranes 1010 is conceived for use within a PM dead-end filtration system 1000 system. In some embodiments, the PM dead-end filtration system 1000 may comprise a plurality of membranes 1010. For example, the system may include a series of cascaded membranes 1010. In some embodiments, the membrane 1010 may be configured to allow at least a portion of the fluid and at least a portion of the of second particles 1008 to permeate through the membrane 1010 and prevent at least a portion of the plurality of first particles 1006 from permeating through the membrane 1010.

In some embodiments, the PM dead-end filtration system 1000 may comprise a channel having an inlet 1012. The inlet 1012 may be configured to receive a suspension 1004 flowing through the system, for example receiving a suspension 1004 flowing from a reservoir 1002. The inlet 1012 may be positioned at one side of the membrane 1010 such that the suspension 1004 may be flowed through the membrane 1010 via the inlet 1012. The inlet 1012 may be tubing or any connecter that connects a source of a suspension 1004 to the membrane 1010. In some embodiments, the PM dead-end filtration system 1000 may comprise a channel having an outlet 1014. The outlet 1014 may be positioned at one side of the membrane 1010 such that the suspension 1004 may be flowed from the membrane 1010. The outlet 1014 may also be tubing or any other connector that may connect the membrane 1010 to permeate storage 1016. In some embodiments, the permeate storage 1016 may be a tank, syringe, fluid bag, cylinder, or any other device that may hold fluid and a plurality of particles.

In some embodiments, the PM dead-end filtration system 1000 may comprise a controller 1018. The controller 1018 may cycle the flow of the fluid in the system from flowing in a forward direction to a reverse direction. For example, in some embodiments, the fluid may flow forward in a direction from inlet 1012, to membrane 1010, to outlet 1014, and the controller 1018 may reverse the flow to flow from outlet 1014, to membrane 1010, to inlet 1012. In some embodiments, these flows may be reversed. For example, the fluid may flow forward in a direction from outlet 1014, to membrane 1010, to inlet 1012, and the reverse flow would be in the opposite direction.

In some embodiments, the controller 1018 may cycle the flow from forward to reverse based on the volumetric flow ratio $$\left(\phi = \frac{V_f}{V_f + V_r}\right)$$

described above. For example, in some embodiments, the controller 1018 may be configured to alter the volumetric flow in a forward direction, the volumetric flow in a reverse direction, or both to achieve a desired volumetric flow ratio for a given system. In some embodiments, the controller 1018 may alter the volumetric flow in either direction by altering the time in which the fluid is passing either in a forward direction or in a reverse direction. As described above, the controller 1018 may also alter the volumetric flow in either direction by altering the velocity (i.e., flow rate, or amplitude of the representative square waves) in either direction. In some embodiments, the volumetric flow in the forward direction is greater than the volumetric flow in the reverse direction. As shown in the above experimental section, if the volumetric flow ratio is 0.50, no net processing would occur because the flux through the membrane 1010 would be equal to the flux back through the membrane 1010. Any volumetric flow ratio between 0.50 and 1.00 is possible with the present systems and methods. The range between 0.50 and 1.00 is exclusive of the endpoints, as a volumetric flow ratio of precisely 0.50 will not net a forward flux through the system, and a volumetric flow ratio of precisely 1.00 is a system with no reverse flow (i.e., no backflush). In some embodiments, the volumetric flow ratio may be from between 0.50 and 1.00; the volumetric flow ratio may be from between 0.55 and 0.95; the volumetric flow ratio may be from between 0.55 and 0.90; the volumetric flow ratio may be from between 0.55 and 0.85; the volumetric flow ratio may be from between 0.55 and 0.80; the volumetric flow ratio may be from between 0.55 and 0.75; the volumetric flow ratio may be from between 0.55 and 0.70; the volumetric flow ratio may be from between 0.55 and 0.65; the volumetric flow ratio may be from between 0.55 and 0.60.

In some embodiment, the controller 1018 may alternate the volumetric flow ratio after each period (one forward cycle and one reverse cycle). For example, it is shown in the model of FIG. 5 that, after each period of cycle from forward to reverse, the next forward cycle will have slightly less solute flux (shown in flux profile 502). This steady increase of forward fluid flux through the system can be attributed to more and more nontargeted particles (first particles 1006) being near the membrane 1010 and less targeted particles (second particles 1008) passing through the membrane 1010; an increasing number of targeted particles (second particles 1008) will have permeated after each subsequent period of cycles. Accordingly, more and more irreversible cake will build up after each subsequent period of cycles. To counteract this decrease in forward flux, the controller 1018 may decrease the volumetric flow ratio after each period of cycles, progressing closer to φ=0.50. Situations may exist wherein an increased volumetric flow rate in each subsequent period of cycles may be desired. For example and not limitation, if after a single period less cake builds, it may be desired to provide a greater volumetric flow in the forward direction in a subsequent period. Such an embodiment is capable within the present systems and methods.

In some embodiments, the controller 1018 may alternate the volumetric flow ratio after each subsequent period of cycles automatically. For example, the controller 1018 may monitor the flow rate through the membrane 1010 at each cycle. When the controller 1018 receives feedback that the forward volumetric flow rate decreases over subsequent cycles, the controller 1018 may decrease the volumetric flow ratio. The controller 1018 may monitor the flow rate through the membrane 1010 by any number of methods, for example and not limitation, by measuring the flow rate of the fluid through the membrane 1010, measuring the permeate flux (second particles 1008) through the membrane 1010, or by measuring a pressure differential from one end of the membrane 1010 to the opposite end. In some embodiments, the controller may increase the volumetric flow ratio after each period (i.e., a subsequent period has a volumetric flow ration closer to 1.00 or full forward flow).

In some embodiments, the controller 1018 may comprise any device capable of flowing fluid in a forward and reverse direction. In some embodiments, the controller 1018 may be a linear actuator, as described above. In some embodiments, the controller 1018 may be a pump capable of flowing the fluid in a forward and reverse direction. In some embodiments, the system may comprise two controllers, for example one controller above the membrane 1010 and proximate the inlet 1012, and one controller below the membrane 1010 and proximate the outlet 1014. In this embodiment, the inlet controller may be configured to flow the fluid in one direction while the outlet controller may be configured to flow the fluid in the opposite direction.

In some embodiments, a PM dead-end filtration system 1000 may use used to control the seed density and uniformity in a profusion bioreactor. Recent advancements in tissue engineering have enabled the use of perfusion bioreactors to grow autograft replacements for repairing trauma to bone, cartilage, tendon, legitimate, and any other tissue. These profusion bioreactors comprise flowing a suspension comprising a fluid and a plurality of cells through a membrane. The membrane comprises a tissue scaffold, such as an extracellular matrix or demineralized bone matrix. As the fluid passes through the tissue scaffold, cells become seeded within the matrix of the tissue scaffold. One problem with current systems is uniformity and seed density through the tissue scaffold. As will be appreciated, as the plurality of cells pass into the tissue scaffold in a forward direction, subsequent cells will have trouble seeding into the tissue scaffold as a layer of cake forms along one end of the tissue scaffold. The systems and methods described herein are a solution to this cell uniformity and density problem.

In some embodiments, the suspension 1004 may comprise a fluid and a plurality of cells. The membrane 1010 may comprise a tissue scaffold. A controller 1018 may cycle the flow of the fluid through the tissue scaffold in a forward and a reverse direction, thus clearing the cake along the inlet 1012 side of the tissue scaffold. The cycling of forward to reverse may be based on the volumetric flow ratio described herein. Also, as described above, because the permeate recovery percentage has a linear relationship to volumetric flow ratio, the system may be designed to produce a desired seeding density. In some embodiments, the PM periodic back flush may be administered to both ends of the tissue scaffold. For example, the controller 1018 may flow the fluid through the tissue in a forward direction in which at least a portion of the fluid flows from the inlet 1012 and through the tissue scaffold, and a reverse direction in which at least a portion of the fluid flows from the outlet 1014 and through the tissue scaffold. In this direction, at least a portion of the plurality of cells will permeate from the inlet 1012 and through the tissue scaffold. The system may then be reversed, where the controller 1018 may flow the fluid through the tissue in a forward direction in which at least a portion of the fluid flows from the outlet 1014 and through the tissue scaffold, and a reverse direction in which at least a portion of the fluid flows from the inlet 1012 and through the tissue scaffold. In this direction, at least a portion of the plurality of cells will permeate from the outlet 1014 and through the tissue scaffold. This embodiment may increase the seeding density and uniformity at both sides of the tissue scaffold. In some embodiments, the tissue scaffold may be removed from the system and repositioned such that a different side of the tissue scaffold is proximate the inlet 1012.

In some embodiments, a PM dead-end filtration system 1000 may use used to improve blood separation. For example, the suspension 1004 may comprise whole blood. The whole blood may comprise white blood cells (the larger first particles 1006) and red blood cells (the smaller second particles 1008). The suspension may further contain a diluent, including and not limited to phosphate buffered saline. A controller 1018 may cycle the flow of the whole blood in a forward direction and a reverse direction based on the volumetric flow ratios described herein. As a result, the recovery percentage of red blood cells will increase according to the volumetric flow ratios described herein.

In some embodiments, a PM dead-end filtration system 1000 may be used to purify samples. For example, in some embodiments, the system may be used to remove conjugated microspheres (second particles 1008) from the aggregated particulates (first particles 1006) resulting from a protein conjugation protocol. Again, the liner relationship between recovery percentage and volumetric flow ratio provides a system where a desired recovery percentage of the microspheres may be achieved by altering the volumetric flow ratio accordingly.

In some embodiments, a PM dead-end filtration system 1000 may be used to improve the sorting efficiencies and recovery percentage of biological samples representative of diagnostic procedures. For example, a sample from a human may be taken, and a clinician or researcher may wish to isolate bacteria from the sample. In many cases, the volume of sample may be small. PM dead-end filtration systems 1000 provide a greater advancement for separating bacteria (second particles 1008) from the small biological sample.

In some embodiments, a PM dead-end filtration system 1000 may be used to deliver molecules to permeabilized cells. As will be appreciated, shear stress can be applied to cells to increase intracellular delivery of molecules into the cells. When shear stress is applied to the cells, the permeability of the cells increases, thereby increasing the intracellular uptake of smaller molecules by the cells. Many clinical and laboratory uses exist for intracellular delivery of molecules into a cell (e.g., into the cytoplasm and/or nucleus of a cell). For example, many reprogramming molecules may be delivered to a cell to modify the function and/or attributes of the cell. The cells that may be manipulated by shear-induced permeabilization include but are not limited to cancer cells, neuron cells, healthy animal cells, or any other cell where molecular manipulation may be beneficial. The types of molecules that may be delivered into a cell via shear-induced permeabilization are vast, and these molecules include but are not limited to macromolecules, nanoparticles, sugars, plasmids, mRNA, enzymes, nucleases, DNA, RNP, antibodies, beads, viruses, immune cells, stem cells, stromal cells, and/or therapeutic cells.

One method of shear permeabilization method includes passing cells through a filtration system, such as the membranes 1010 discussed herein. In some embodiments, the cells may be suspended within a cell medium also capable of passing through the membrane 1010. Any membrane 1010 described herein or otherwise known in the art may be used for shear permeabilization. For example and not limitation, the membrane may be a fibrous membrane, patterned microsieve membrane, pillar membrane, trap membrane, weir membrane, a tissue, or a membrane comprising microchannels. In some embodiments, the molecules that are intended to be administered into the cells may also be suspended in the cell medium along with the cells. The molecules are inherently smaller than the cells, so the molecules may also pass through the membrane 1010. In some embodiments, the molecules may be administered to the cells after PM filtration in a separate process.

In some embodiments, PM dead-end filtration may provide an advantageous system for shear permeabilization due to the nature of the forward to reverse flow through a membrane 1010. For example, the systems and methods described herein utilize membranes 1010 capable of inducing the shear stresses needed to permeabilize cells as the cells pass through the membrane 1010. In some embodiments, a controller may cycle the flow of the cell medium containing cells (or cells and molecules) in a forward direction and in a reverse direction. In the forward direction, at least a portion of the cells and molecules may permeate through an inlet 1012, through the membrane 1010, and to an outlet 1014. Also, as shown in FIGS. 4-5, in PM dead-end filtration, at least a portion of permeate (or targeted particles 118, which may be cells) may pass through a membrane 1010 (e.g., filtration surface 116 in FIG. 4) in the forward flow direction and pass through the membrane 1010 again in a reverse flow direction (reverse flux of the cells). Accordingly, a portion of the permeate passing through the membrane 1010 in a reverse direction may be subjected to additional shears. In some embodiments, once a cell passes through the membrane 1010, the shear stress provided by the membrane 1010 may permeabilize the permeated cells. Once permeated, the cells may have an increased degree of intracellular uptake of the molecules. Additionally, each system and method associated with PM dead-end filtration described herein may be used to increase the enrichment factor of permeabilized cells and the recovery percentage of permeabilized cells, for example altering the volumetric flow ratio and/or volumetric flow rate.

Other uses for pulse-modulated period backflush are conceived, and the other uses will be apparent to those of ordinary skill in the art upon reviewing the systems and methods described herein.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A filtration system comprising:
a channel having an inlet and an outlet;
a membrane positioned within the channel between the inlet and the outlet; and
a controller configured to cycle a flow of a volume of fluid based on a volumetric flow ratio from flowing in a forward direction through the membrane at a volume of fluid flow $V_f$, to flowing in a reverse direction through the membrane at a volume of fluid flow $V_r$;
wherein the forward direction of fluid flow is the direction from the inlet toward the membrane;
wherein the reverse direction of fluid flow is the direction from the outlet toward the membrane; and
wherein the volumetric flow ratio is equal to $$\frac{V_f}{V_f + V_r}.$$

2. The filtration system of claim 1 further comprising:
a suspension comprising the fluid, first particles, and second particles, the mean size of the first particles larger than the mean size of the second particles;
wherein the membrane is configured to allow at least a portion of the fluid and a portion of the second particles of the suspension flowing in the forward direction to permeate through the membrane; and
wherein the membrane is configured to prevent at least a portion of the first particles of the suspension flowing in the forward direction to permeate through the membrane.

3. The filtration system of claim 1, wherein the volumetric flow ratio is from between 0.5 and 1.00.

4. The filtration system of claim 1, wherein the volumetric flow ratio is from between 0.55 and 0.80.

5. The filtration system of claim 1, wherein the controller is further configured to perform two or more cycles and to vary at least one of a volumetric flow rate of the fluid in the forward direction or a volumetric flow rate of the fluid in the reverse direction from a first cycle to a subsequent second cycle.

6. The filtration system of claim 1, wherein the controller is further configured to perform two or more cycles and to increase a volumetric flow rate of the fluid in the reverse direction from a first cycle to a subsequent second cycle.

7. The filtration system of claim 1, wherein the membrane comprises at least one of a fibrous membrane, patterned microsieve membrane, pillar membrane, trap membrane, or weir membrane.

8. The filtration system of claim 1, wherein the membrane comprises a tissue.

9. The filtration system of claim 8, wherein the tissue comprises at least one of an extracellular matrix or a bone matrix.

10. The filtration system of claim 1, wherein the controller is further configured to perform two or more cycles and to decrease the volumetric flow ratio in each subsequent cycle.

11. The filtration system of claim 1, wherein the inlet is configured to receive a suspension, the suspension comprising the fluid, first particles, and second particles; and
wherein the controller is further configured to perform two or more cycles and to monitor an amount of the second particles permeating through the membrane during flow in the forward direction of a first cycle, and based on the monitored amount, vary during a subsequent second cycle at least one of:
the volumetric flow ratio;
the flow rate in the forward direction;
the flow rate in the reverse direction;
a duration of flow in the forward direction; or
a duration of flow in the reverse direction.

12. The system of claim 11, wherein the volumetric flow ratio is from between 0.5 and 1.00;
wherein the controller is further configured to vary at least one of the volume of fluid flow $V_f$ or the volume of fluid flow $V_r$ from the first cycle to the subsequent second cycle; and
wherein in at least one of the cycles, the volume of fluid flow $V_f$ and volume of fluid flow $V_r$ are not the same.

13. The filtration system of claim 11, wherein a first side of the membrane proximate the inlet of the channel comprises a cake layer comprising the first particles and the second particles; and
wherein the suspension flowing in the reverse direction is configured to break apart at least a portion of the cake layer.

14. The filtration system of claim 11, wherein the suspension comprises whole blood;
wherein the first particles are white blood cells; and
wherein the second particles are red blood cells.

15. The filtration system of claim 14, wherein the suspension further comprises a diluting agent.

16. The filtration system of claim 11, wherein the second particles are bacterial cells.

17. The filtration system of claim 11, wherein the first particles are aggregated particulates resulting from a protein conjugation protocol and the second particles are conjugated microspheres.

18. A method of filtering particles comprising:
providing the suspension into the inlet of the channel of the filtration system of claim 2; and
cycling a flow of the suspension at the volumetric flow ratio through the filtration system between the forward direction and the reverse direction.

19. The method of claim 18, wherein the volumetric flow ratio is from between 0.5 and 1.00.

20. The method of claim 18, wherein the volumetric flow ratio is from between 0.55 and 0.80.

21. The method of claim 18, wherein the volumetric flow ratio decreases in each subsequent cycle.

22. The method of claim 18, wherein the first particles are aggregated particulates resulting from a protein conjugation protocol and the second particles are conjugated microspheres.

23. The method of claim 18 further comprising:
monitoring an amount of the second particles permeating through the membrane during flow of the suspension in the forward direction of a first cycle; and
varying during a subsequent second cycle, based on the monitored amount, at least one of:
the volumetric flow ratio;
the flow rate in the forward direction;
the flow rate in the reverse direction;
a duration of flow in the forward direction; and
a duration of flow in the reverse direction.

24. The method of claim 18, wherein the volumetric flow ratio has a linear relationship to a recovery percentage for a portion of the second particles permeating through the membrane; and
wherein the method further comprises:
calculating the recovery percentage of the second particles permeating through the membrane at a plurality of volumetric flow ratios;
identifying a desired permeation amount for a portion of the second particles based on the recovery percentage;
calculating a desired volumetric flow ratio based on the linear relationship;
adjusting the volumetric flow ratio to equal the desired volumetric flow ratio; and
recovering the desired permeation amount for the portion of the second particles.

25. A method of controlling seed density and uniformity comprising:
cycling the suspension through the filtration system of claim 2;
wherein the filtration system is a profusion bioreactor;
wherein the membrane comprises a tissue scaffold; and
wherein the first and second particles are cells.

26. The method of claim 25, wherein the tissue scaffold comprises at least one of an extracellular matrix or a bone matrix.

27. A method of delivering molecules into a permeated cell comprising:
cycling the suspension through the filtration system of claim 2, wherein the fluid is a cell medium, the first particles are cells, and the second particles are molecules, and wherein the permeation of the permeated cells through the membrane applies a shear stress to the permeated cells;
permeabilizing, via the shear stress, the permeated cells that pass through the membrane; and
delivering at least one molecule into one of the permeabilized cells.

28. The method of claim 27, wherein the molecules are selected from the group consisting of macromolecules, nanoparticles, sugars, plasmids, mRNA, enzymes, nucleases, DNA, RNP, antibodies, beads, viruses, immune cells, stem cells, stromal cells, and therapeutic cells.

* * * * *